United States Patent [19]
Burbank et al.

[11] Patent Number: 5,997,524
[45] Date of Patent: Dec. 7, 1999

[54] CATHETER ASSEMBLY FOR PERCUTANEOUS ACCESS TO SUBCUTANEOUS PORT

[75] Inventors: Jeffrey H. Burbank, Boxford; James M. Brugger, Newburyport, both of Mass.; C. David Finch, Clinton, Miss.

[73] Assignee: Vasca, Inc., Tewksbury, Mass.

[21] Appl. No.: 08/896,790

[22] Filed: Jul. 18, 1997

[51] Int. Cl.⁶ ..................................................... A61M 5/32
[52] U.S. Cl. ........................... 604/506; 604/502; 604/93; 604/264
[58] Field of Search ............................. 604/1–3, 93, 264, 604/265, 272–274, 49–53

[56] References Cited

U.S. PATENT DOCUMENTS

| | | |
|---|---|---|
| 2,693,186 | 11/1954 | Riker et al. . |
| 2,847,995 | 8/1958 | Adams . |
| 3,134,380 | 5/1964 | Armao . |
| 4,243,035 | 1/1981 | Barrett . |
| 4,464,178 | 8/1984 | Dalton . |
| 4,569,675 | 2/1986 | Prosl et al. . |
| 4,645,495 | 2/1987 | Villancouet . |
| 4,710,174 | 12/1987 | Moden et al. . |
| 4,775,369 | 10/1988 | Schwartz . |
| 4,778,452 | 10/1988 | Moden et al. ............................ 604/93 |
| 4,861,341 | 8/1989 | Woodburn ............................... 604/175 |
| 4,886,502 | 12/1989 | Poirier et al. ........................... 604/175 |
| 4,955,861 | 9/1990 | Enegren et al. . |
| 5,041,098 | 8/1991 | Loiterman et al. . |
| 5,059,186 | 10/1991 | Yamomato et al. ..................... 604/280 |
| 5,176,653 | 1/1993 | Metais .................................... 604/167 |
| 5,421,814 | 6/1995 | Geary . |
| 5,562,617 | 10/1996 | Finch, Jr. et al. . |
| 5,725,497 | 3/1998 | Woodruff et al. ......................... 604/49 |

*Primary Examiner*—John D. Yasko
*Assistant Examiner*—Deborah Blyveis
*Attorney, Agent, or Firm*—Townsend and Townsend and Crew LLP

[57] ABSTRACT

An access catheter for percutaneously connecting to a subcutaneously implanted port comprises a catheter body having a distal end and a proximal end. A needle or other access tube is connected to the distal end of the catheter body through a fitting, optionally at a right angle relative to the catheter body. A compressible element impregnated with an antiseptic, antibiotic, anesthetic, or other active agent, is provided adjacent the distal end of the catheter body and surrounding the needle. When the needle is percutaneously introduced to the port, the compressible element will be compressed to express the agent onto the skin surface surrounding the penetration site.

36 Claims, 4 Drawing Sheets

CATHETER ASSEMBLY FOR PERCUTANEOUS ACCESS TO SUBCUTANEOUS PORT

BACKGROUND OF THE INVENTION

1. Field of the Invention

The present invention relates generally to the design and use of medical devices, and more particularly to the design and use of a needle assembly for percutaneously accessing an implantable port connected to a patient's vascular system or other body lumen.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications, such as intravenous feeding, intravenous drug delivery, and which are limited in time, they are not suitable for hemodialysis and other extracorporeal procedures that must be repeated periodically, often for the lifetime of the patient.

For hemodialysis and other extracorporeal treatment regimens, a variety of implantable ports have been proposed over the years. Typically, the port includes an internal chamber and an access region, such as a septum, while the chamber is attached to an implanted catheter which in turn is secured to a blood vessel. In the case of veins, the catheter is typically indwelling and in the case of arteries, the catheter may be attached by conventional surgical techniques.

Of particular interest to the present invention, implantable ports typically include a needle-penetrable septum which permits the percutaneous penetration of a needle into the internal chamber. The chamber, in turn, is connected to one end of the catheter, and the other end of the catheter is indwelling in the blood vessel. While workable, such designs suffer from a number of problems. Repeated penetration of the septum often leads to degradation over time, presenting a substantial risk of small particulates entering the blood stream and/or need to periodically replace the port. The fragility of the septum has necessitated the use of relatively small bore needles, typically 19 gauge needles (having an outside diameter below 1.08 mm and a bore diameter below 0.94 mm) or smaller. Such small needles significantly limit the flow volume that can be delivered to and from the port. While this may not be problematic in drug delivery, it is of concern in high volume applications, such as dialysis, hemofiltration, and the like.

As an alternative to septum-based implantable ports, the assignee of the present application has developed an implantable port having a mechanical valve which replaces the septum component on the septum ports. The valve is actuated by the percutaneous introduction of the needle through an aperture on the valve housing. Since the septum has been eliminated, the needle used to access and actuate such ports having mechanical valves can be much larger than those used to penetrate septums, typically having a size of at least 16 gauge (having an outside diameter of 1.66 mm and a bore size up to 1.5 mm), preferably higher. The use of a larger access needle will permit a much higher volumetric transfer rate for blood or other liquids to be transferred, such as infusates, perfusates, dialysis fluids, and the like.

Heretofore, the assignee of the present application has generally utilized straight needles for accessing the implantable ports having mechanical valves. By "straight needle," it is meant that the needle is aligned parallel to or coaxial with the distal end of the catheter to which it is attached. Such a straight needle attachment can be problematic, particularly since it results in a "high profile" catheter attachment to the skin. The needle or other access tube inserted into the port will generally be oriented in a direction normal to the patient's skin. Thus, the catheter will generally project straight out from the patient's skin, making immobilization of the catheter during use problematic.

For these reasons, it would be desirable to provide access catheter systems capable of vertically accessing an implantable port and incorporating large bore needles to accommodate high fluid transfer rates. Such catheters should be inexpensive to produce, have highly reliable designs, and be compatible with other aspects of the present invention as described below.

A second problem with access catheters and needles relates to the maintenance of sterility. Generally, the patient's skin will be swabbed with alcohol or other disinfectant prior to percutaneous introduction of a needle or other access tube. While such precautions are generally sufficient to prevent infection, the need to repeatedly access the same percutaneous insertion site presents significant risk of infection to the patient.

It would thus be desirable to provide improved access catheters and methods which enhance sterility and inhibit infection resulting from percutaneous needle access. Such apparatus and methods will preferably be capable of delivering a desired antiseptic, antibiotic, anesthetic, or other active agent to the tissue location through which the needle is inserted. Preferably, the apparatus and methods will provide for a prolonged delivery of the desired agents over time, preferably over the entire time period over which the needle is to be maintained in the access port.

At least certain of these objective will be met by the invention described below.

2. Description of the Background Art

Hypodermic needles having absorbent pads carrying an antiseptic are described in U.S. Pat. Nos. 4,243,035; 3,134,380; and 2,693,186. Needles having compressible sheaths for maintaining sterility are described in U.S. Pat. Nos. 4,775,369 and 2,847,995. Needles and other access tubes for percutaneously accessing implanted ports are described in U.S. Pat. No. 5,562,617, as well as co-pending application Ser. Nos. 08/539,105; 08/724,948; 60/036,124; and 08/856,641 (Attorney Docket No. 17742-001700; filed on May 15, 1997), assigned to the assignee of the present application, the full disclosures of which are incorporated herein by reference. Needles and other structures connected and/or connectable to catheters at generally right angles for accessing implanted ports are described in U.S. Pat. Nos. 5,421,814; 5,041,098; 4,955,861; 4,710,174; 4,645,495; 4,464,178; and 4,569,675.

SUMMARY OF THE INVENTION

The present invention provides improved access catheters for percutaneous attachment to implanted ports, particularly with implanted ports having internal isolation valves of the type described in co-pending application Ser. No. 60/036,124, the full disclosure of which has previously been incorporated herein by reference. The access catheters of the present invention are capable of delivery antiseptics, antibiotics, anesthetics, wound healing agents, and other active agents to the percutaneous penetration site through which the catheter is attached to the implanted port. The ability to delivery such drugs to the penetration site is particularly advantageous in inhibiting infection while the access catheters are connected to the port for prolonged periods of time. The access catheters may also be optimally configured for low profile connection to the port, even when the access catheters comprise relatively large bore access needles/tubes for percutaneous insertion into the implanted ports. The combination of active agent delivery and low profile connection is particularly useful for long term access, e.g. over four hours, since both patient safety and comfort are enhanced.

According to a first aspect of the apparatus of the present invention, an access catheter comprises a flexible catheter body having a proximal end and a distal end. The catheter body typically has a length in the range from 10 cm to 30 cm, preferably from 12 cm to 18 cm, and a lumenal diameter in the range from 1 mm to 5 mm, usually from 3.4 mm to 4.6 mm. A fitting is secured to the distal end of the catheter body, and a rigid access tube extends from the fitting and is fluidly connected to the lumen of the catheter body so that the catheter can be connected to an implanted port via the access tube. A compressible element is secured against the fitting and surrounds at least a portion of the access tube. The compressible element is impregnated with an active agent, including any of the agents listed above, which is expressed from the compressible element as the element is compressed against a patient's skin when the access tube is percutaneously inserted into an implanted port. By surrounding the tube and being placed directly over the percutaneous penetration, the antiseptics, antibiotics, anesthetics, or other active agents will be delivered directly to the tissue which is being compromised by the penetration of the access tube. Usually, the catheter will further comprise a connector at the proximal end of the flexible catheter body, although in some cases the catheter body could be directly connected to a fluid source or receptacle without the need for a connector or other proximal fitting.

Preferably, the rigid access tube will be straight and will have a length in the range from 15 mm to 40 mm, preferably from 18 mm to 26 mm. The access tube will usually have a relatively large bore, typically in the range from 1 mm to 2.5 mm, preferably from 1.5 mm to 2.1 mm, and the preferred access tube is a fistula-type coring needle, commonly referred to as a fistula needle. The large bore access tube is advantageous in minimizing flow resistance between the implanted port and the catheter. Such large access tubes, typically needles having sharpened distal tips, are disadvantageous since they increase the risk of infection when percutaneously introduced to the patient. They are also more difficult to maintain in place when emerging from the patient's skin. The present invention provides for direct delivery of antiseptics, antibiotics, anesthetics, and the like, to decrease the risk of infection and further provides for low profile connection of the catheter to decrease the risk of dislodging the catheter access needle while in use.

The compressible element may comprise any one of a variety of structures capable of containing and selectively delivering the antiseptic, antibiotic, anesthetic, and other active agents, which will typically be in the form of liquids, solutions, gels, or the like. Exemplary compressible elements include open cell foams, e.g. "sponges," fibrous wads, bellows structures, and the like. The amount of liquid agent held within the compressible element will typically be in the range from 5 $\mu$l to 0.5 ml, usually from 0.05 ml to 0.2 ml.

According to a second aspect of the apparatus of the present invention, an access catheter comprises a flexible catheter body, a fitting, and a rigid access tube generally as described above. According to the present invention, the rigid access tube is disposed in the fitting at a generally right angle relative to the distal end of the catheter body. Such a configuration permits the access tube to be percutaneously introduced into an implanted port while the catheter body remains generally parallel to or flat against the patient's skin. Such a "low profile" orientation of the catheter is advantageous since it reduces the risk of dislodgement, is more comfortable to the patient, and is generally easier to accommodate in a crowded medical therapy location. Such low profile access catheters may optionally incorporate the compressible element of the present invention as described above.

Methods according to the present invention for accessing a subcutaneously implanted port comprise providing an access catheter having a compressible element, generally as described above. The access tube of the access catheter is percutaneously inserted through a patient's skin, optionally through a tissue tract which has been previously formed and into an aperture on the implanted port. Preferably, the aperture will comprise a tapered cylindrical surface which reduces in size to seal against the needle as it is introduced. The needle may thus be a conventional untapered design yet still achieve a fluid-tight seal by simply inserting it into the port. The tapered aperture is described in co-pending application Ser. No. 08/036,124. The compressible element is compressed sufficiently to release the antibiotic or other active agent against the patient's skin in order to maintain sterility and reduce the risk of infection.

In another aspect of the method of the present invention, an access catheter comprising a rigid access tube oriented at a generally right angle relative to the flexible catheter body is provided. The access tube is percutaneously inserted through a patient's skin into the implanted port where the flexible catheter body is maintained in a generally parallel or flat orientation against the patient's skin. Usually, the access tube is percutaneously inserted to a depth which results in the flexible catheter body lying at a height above the patient's skin from 0 cm to 1 cm.

The present invention further provide kits which comprise an access catheter, generally as described above, in combination with instructions for use (IFU) and a convention package. The instructions for use will set forth any of the methods described above.

DESCRIPTION OF THE SPECIFIC EMBODIMENTS

Figure 1:
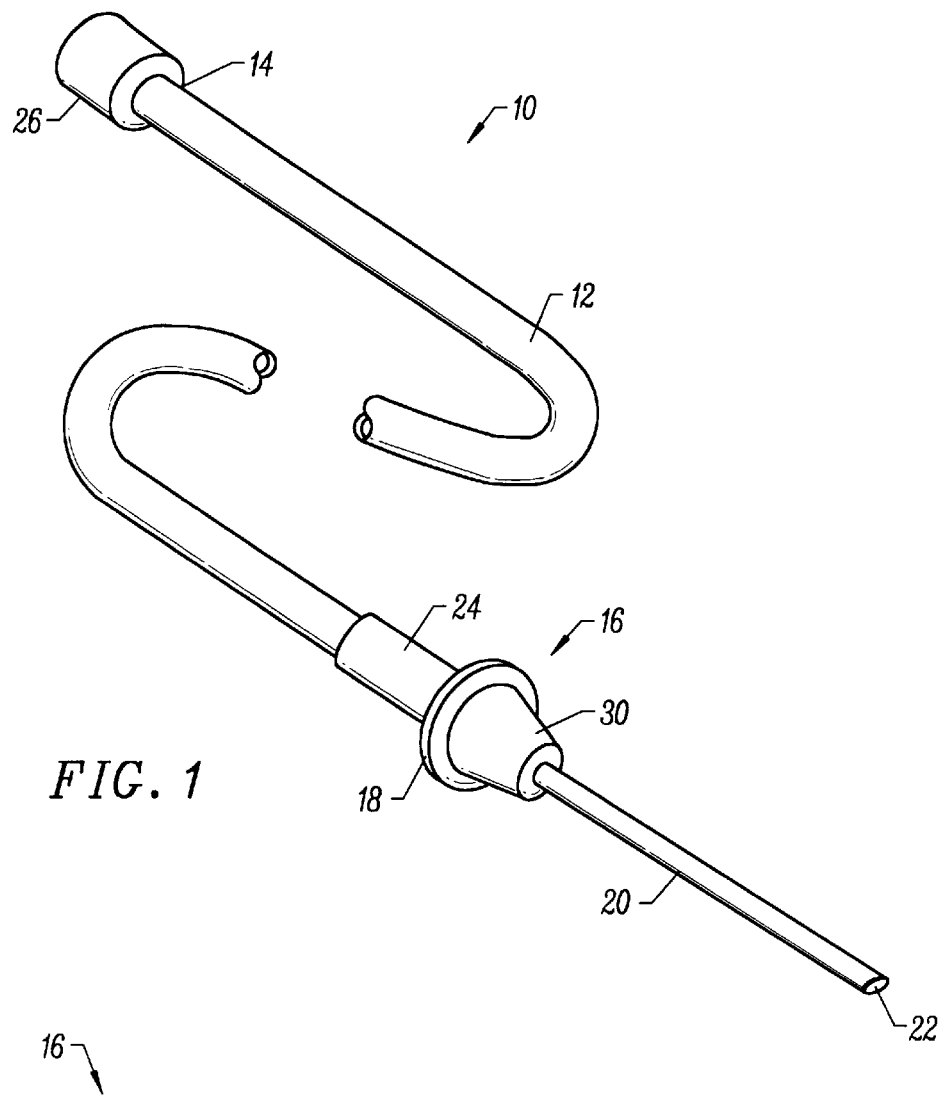
FIG. 1 is a perspective view of a first embodiment of the access catheter of the present invention.
Figure 2:
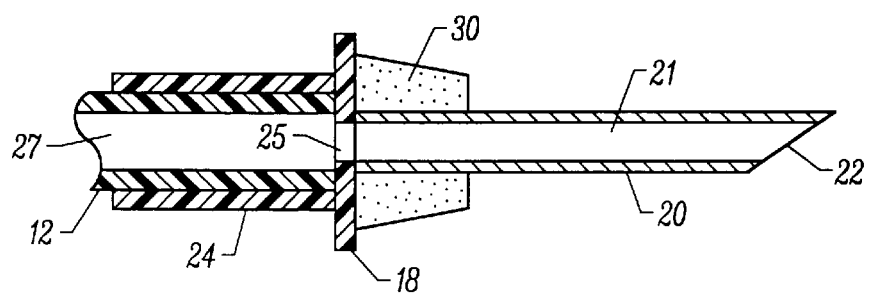
FIG. 2 is a detailed view of the distal end of the catheter of FIG. 1, shown in section.

Referring now to FIGS. 1 and 2, an access catheter 10 constructed in accordance with the principles of the present invention comprises a catheter body 12 having a proximal end 14 and a distal end 16. The catheter body 12 will typically comprise a flexible polymer tube, composed of a medically compatible organic polymer, such as polyvinylchloride, and having the dimensions set forth above. Such polymeric tubes may be formed by extrusion and will typically include a single lumen extending the entire length from the proximal end 14 to the distal end 16.

A fitting 18 is secured to the distal end 16 of the catheter body 12, typically by an adhesive, heat welding, solvent bonding, penetrating fasteners (not shown), or other conventional means. The fitting is shown as a generally flat disc but could have a variety of alternative geometries. An access tube 20, typically a needle having a sharpened distal tip 22 extends distally from the side of the fitting 18 opposite to that to which the catheter body 12 is attached. A stress relief sleeve 24 will usually be provided at the connection of the distal end 16 of the catheter body 12 to the fitting 18. The access tube 20 has a lumen 21, and the dimensions of the access tube are generally as set forth above. Usually, the access tube will be composed of a metal, such as stainless steel, but could also be formed from a hard plastic. The preferred needle is a large bore coring needle, such as a fistula needle, having a bore of at least 1.16 mm (16G), usually at least 1.33 mm (15G), more usually at least 1.55 mm (14G), still more usually at least 1.73 mm (13G) and sometimes as large as 2.08 mm (12G), or larger. By "coring" needle, it is meant that the needle will be able to core tissue as advanced therethrough. The use of small bore non-coring needles, such as Huber needles, and stylets is generally not preferred in the apparatus and methods of the present invention. Although not illustrated, the access tube 20 could also have a blunt end, as described below in connection with FIGS. 5A and 5B. An orifice 25 will be provided in the fitting 18 and generally be aligned with the lumen 21, thus opening into lumen 27 in the catheter body. A particular advantage of the illustrated construction is that the access tube 20 has a relatively large lumenal diameter and the connection to the catheter body 12 minimizes flow resistance. Usually, a connector 26, such as a luer connector, is provided at the proximal end of the catheter body 12. Such a connector, however, is not necessary and is possible to directly connect the catheter body to a desired treatment device, fluid source, or other external apparatus.

A compressible element 30 is attached at the distal end 16 of the catheter body. Preferably, the compressible element 30 is attached on a distal side of the fitting 18 so that it is coaxially disposed about the proximal end of the access tube 20. In this way, as the compressible element 30 is compressed (upon percutaneous insertion of the needle as described in more detail below), material impregnated within the element 30 is expressed onto the patient's skin. The compressible element 30 may have a variety of specific structures, generally as described above. As illustrated in FIG. 1 and 2, the compressible element 30 is an open cell foam or "sponge" structure which is impregnated with the antiseptic, antibiotic, anesthetic, or other active agent to be delivered, typically by absorption. The compressible element 30 may be saturated with the active agent in liquid form so that an initial "bolus" of the liquid agent is released immediately when the access tube is introduced. Thereafter, the remaining amount of active agent will be released more slowly while the access tube remains in place.

Figure 3:
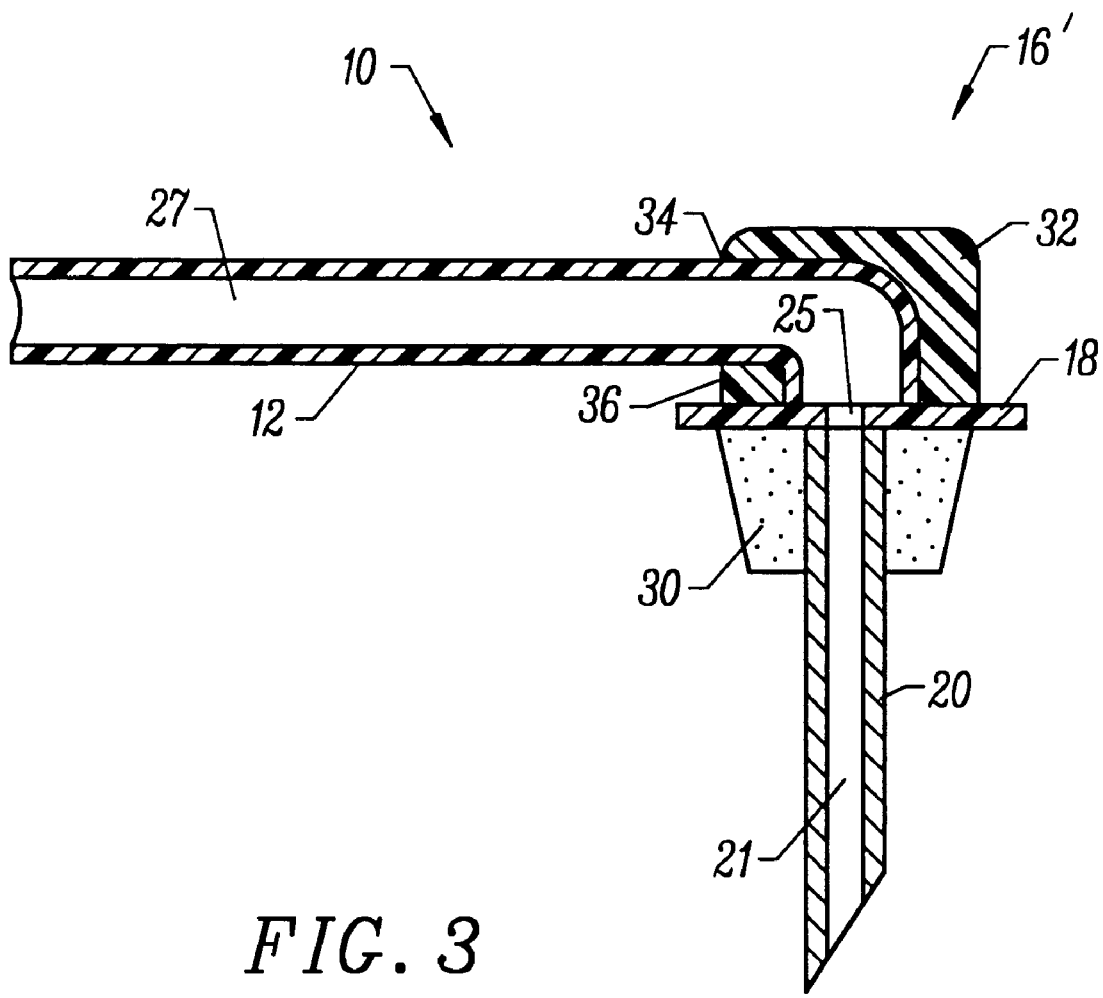
FIG. 3 is a detailed view of an alternative distal end of the catheter of FIG. 1, shown in section.

Referring now to FIG. 3, an alternative configuration 16' of the distal end of catheter 10 orients the access tube 20 at an approximately right angle (90°) relative to the distal end of the catheter body 12. The fitting 18 includes a cap 32 which defines a 90° bend with an inlet 34 receiving the distal end of catheter body 12 and an outlet 36 connected to the fitting 18. The catheter body 12 can extend through the internal passage of cap 32 or, alternatively, may be secured at the inlet end. In either case, the substantially continuous lumen 27 is created through the catheter body 12 to the orifice 25 and the fitting 18 and thus to the lumen 21 of access tube 20.

Figure 4A:
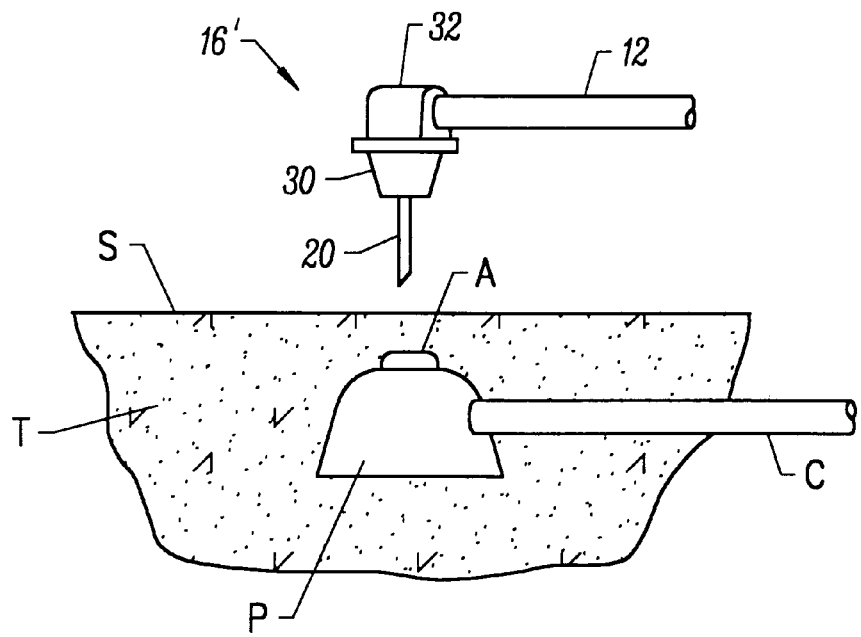
FIGS. 4A and 4B illustrate use of the catheter of FIG. 3 for accessing an implanted port according to the method of the present invention.
Figure 4B:
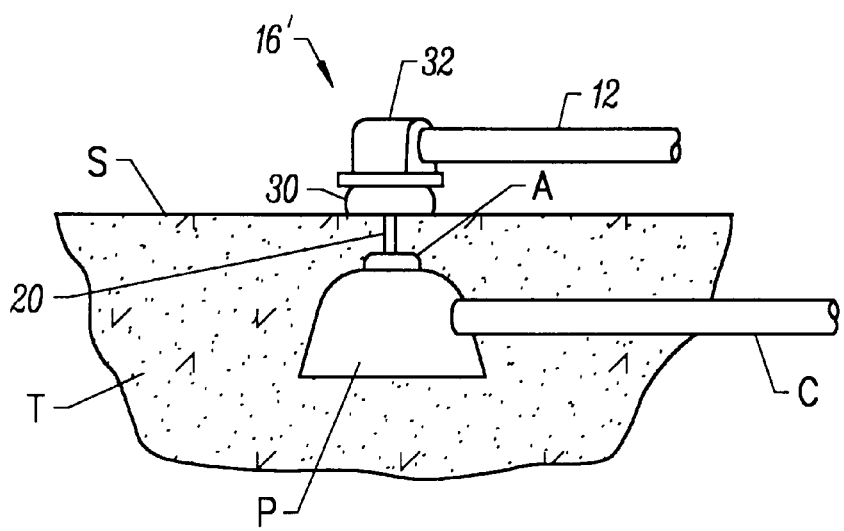

Referring now to FIGS. 4A and 4B, use of the catheter 10 having the distal end 16' for accessing an implanted port P will be described. The port may be constructed as described in co-pending application Ser. No. 60/036,124, the full disclosure of which is incorporated herein by reference. Detailed methods for percutaneously introducing large bore access needles to subcutaneously implanted ports are described in co-pending Application filed on the same day as the present application, the full disclosure of which is incorporated herein by reference. Briefly, the port P includes an entrance aperture A adapted to receive a needle or other access tube in a generally vertical orientation through the patient's skin S. That is, the port P will be implanted so that the aperture A is aligned to receive the access tube 20 in a direction which is generally normal or perpendicular to the surface of the patient's skin at that point. After entering the port P, the access tube 20 will actuate an internal valve (not shown) to open a flow path with a lumen in cannula C, where the cannula may be connected to a blood vessel or other body lumen, as described in co-pending application Ser. No. 08/856,641 (Attorney Docket No. 17742-001700), filed on May 15, 1997.

The distal end 16' of catheter 10 is aligned so that access tube 20 is positioned over the aperture A. This may be done by manually feeling the perimeter of port P through the patient's skin. Conveniently, the aperture A will be located in the center of the top of port P, making alignment of the access tube 20 relatively simple. The access tube 20 has a sharpened distal tip which can be percutaneously penetrated through the skin S and tissue T overlying the aperture A. The aperture will typically be from 3 mm to 15 mm beneath the surface of the skin S.

The access tube 20 is introduced through the aperture A by a distance sufficient to compress the compressible element 30 as shown in FIG. 4B. Such compression will express the liquid active agent which has been impregnated in the compressible element 30, typically an antibiotic, antiseptic, anesthetic, growth factor, or the like. The liquid agent will spread over the surface of the skin S and will also penetrate at least partly into the tissue tract formed by the access needle 20 as it enters the aperture A.

After the catheter has been introduced, as shown in FIG. 4B, catheter body 12 will lie generally parallel to and flat over the surface of the patient's skin S. Such low profile configuration is advantageous since it reduces the risk of accidentally dislodging the catheter. It also facilitates management and routing of the catheter in the crowded patient environment.

Figure 5:
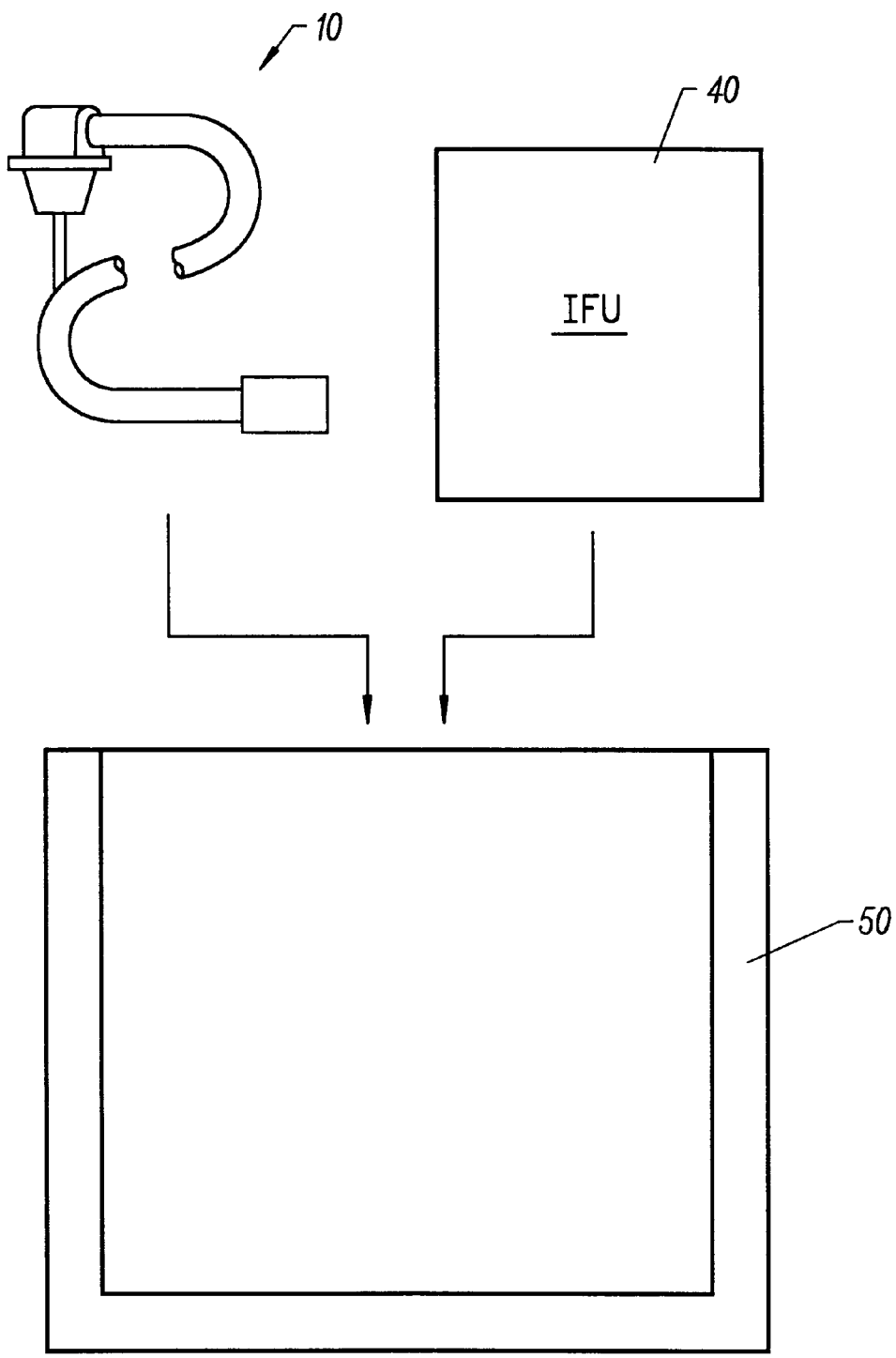
FIG. 5 illustrates a kit according to the present invention comprising an access catheter, a package, and instructions for use.

An access catheter according to the present invention may be packaged together with instructions for use (IFU) in a kit, as shown in FIG. 5. A conventional package, which may be a pouch 50 or any other suitable package, such as a tray, box, tube, or the like, may be used to contain the access catheter and IFU 40, where the IFU may be printed on a separate sheet and/or may be printed on the packaging itself. Optionally, but not necessarily, the access catheter 10 may be sterilized within the package, e.g. by radiation or ethyleneoxide. The instructions will set forth any of the aspects of the method of the present invention described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An access catheter comprising:
   a flexible catheter body having a proximal end and a distal end;
   a fitting secured to the distal end of the catheter body;
   a rigid access tube having a base adjacent to the fitting and being fluidly connected to the catheter body and extending from the fitting; and
   a compressible element secured to the fitting at the base of the rigid access tube and surrounding the base of the rigid access tube and impregnated with an active agent which is expressed from the element as the element is compressed.

2. An access catheter as in claim 1, further comprising a connector at the proximal end of the flexible catheter body.

3. An access catheter as in claim 1, wherein the catheter body has a length in the range from 10 cm to 30 cm and a lumenal diameter in the range from 1 mm to 5 mm.

4. An access catheter as in claim 3, wherein the rigid access tube is straight, has a length in the range from 15 mm to 40 mm, and a lumenal diameter in the range from 1 mm to 2.5 mm.

5. An access catheter as in claim 1, wherein the rigid access tube is a coring needle.

6. An access catheter as in claim 1, wherein the rigid access tube has a blunt distal tip.

7. An access catheter as in claim 1, wherein the compressible element comprises a material selected from the group consisting of open cell foams, fibrous wads, and bellows structures.

8. An access catheter as in claim 1, wherein the active agent is selected from the group consisting of antibiotics, antiseptics, anesthetics, and growth factors.

9. An access catheter as in claim 1, wherein the rigid access tube is disposed in the fitting at a generally right angle relative to the distal end of the catheter body.

10. An access catheter comprising:
    a flexible catheter body having a proximal end and a distal end;
    a fitting secured to the distal end of the catheter body; and
    a rigid access tube fluidly connected to the catheter body and extending from the fitting, wherein the rigid access tube is straight, has a length in the range from 15 mm to 40 mm, and a lumenal diameter in the range from 1 mm to 5 mm;
    wherein the rigid access tube is disposed in the fitting at a generally right angle relative to the distal end of the catheter body.

11. An access catheter as in claim 10, further comprising a connector at the proximal end of the flexible catheter body.

12. An access catheter as in claim 10, wherein the catheter body has a length in the range from 10 cm to 30 cm and a lumenal diameter in the range from 1 mm to 5 mm.

13. An access catheter as in claim 10, wherein the rigid access tube is a coring needle.

14. An access catheter as in claim 10, wherein the rigid access tube has a blunt distal tip.

15. An access catheter as in claim 10, further comprising a compressible element secured to the fitting about a base of the rigid access tube and impregnated with an active agent which is expressed from the element as the element is compressed.

16. An access catheter as in claim 15, wherein the compressible element comprises a material selected from the group consisting of open cell foams, fibrous wads, and bellows structures.

17. An access catheter as in claim 15, wherein the active agent is selected from the group consisting of antibiotics, antiseptics, anesthetics, and growth factors.

18. An access catheter as in claim 10, wherein the rigid access tube is a fistula-type needle.

19. A method for percutaneously accessing a subcutaneously implanted port, said method comprising:
    providing an access catheter having a flexible catheter body and a rigid access tube at a distal end thereof; and
    percutaneously inserting the access tube through a patient's skin into the implanted port;
    wherein a compressible element disposed on the rigid access tube is compressed to express an active agent against the patient's skin.

20. A method as in claim 19, wherein the compressible element is compressed between the patient's skin and a fitting secured to a distal end of the catheter body.

21. A method as in claim 19, wherein the compressible element comprises a material selected from the group consisting of open cell foams, fibrous wads, and bellows structures.

22. A method as in claim 19, wherein the active agent is selected from the group consisting of antibiotics, antiseptics, anesthetics, and growth factors.

23. A method as in claim 19, wherein the access tube is disposed at a generally right angle relative to the distal end of the flexible catheter body.

24. A method as in claim 23, wherein the access tube is percutaneously inserted at an angle normal to the skin surface through which it is inserted, wherein the flexible catheter body will lie generally flat against the skin surface.

25. A method as in claim 24, wherein the access tube is percutaneously inserted to a depth which results in the lying at a height from 0 cm to 1 cm above the skin surface.

26. A method as in claim 19, wherein access is maintained for at least four hours.

27. A method for percutaneously accessing a subcutaneously implanted port, said method comprising:
    providing an access catheter having a flexible catheter body and a rigid access tube at a distal end thereof; and
    percutaneously inserting the access tube through a patient's skin into the implanted port, wherein the rigid access tube is straight, has a length in the range from 15 mm to 40 mm, and a lumenal diameter in the range from 1 mm to 5 mm;
    wherein the access tube is disposed at a generally right angle relative to the distal end of the flexible catheter body.

28. A method as in claim 27, wherein the access tube is percutaneously inserted at an angle normal to the skin surface through which it is inserted, wherein the flexible catheter body will lie generally flat against the skin surface.

29. A method as in claim 28, wherein the access tube is percutaneously inserted to a depth which results in the lying at a height from 0 cm to 1 cm above the skin surface.

30. A method as in claim 27, wherein the access needle is non-tapered and is inserted into a tapered aperture on the port to form a seal.

31. A method as in claim 27, wherein a compressible element disposed on the rigid access tube is compressed to express an active agent against the patient's skin.

32. A method as in claim 31, wherein the compressible element is compressed between the patient's skin and a fitting secured to a distal end of the catheter body.

33. A method as in claim 31, wherein the compressible element comprises a material selected from the group consisting of open cell foams, fibrous wads, and bellows structures.

34. A method as in claim 31, wherein the active agent is selected from the group consisting of antibiotics, antiseptics, anesthetics, and growth factors.

35. A method as in claim 27, wherein the rigid access tube is a fistula-type needle.

36. A method as in claim 27, wherein access is maintained for at least four hours.

* * * * *